US009433395B2

(12) United States Patent
Kang et al.

(10) Patent No.: US 9,433,395 B2
(45) Date of Patent: Sep. 6, 2016

(54) X-RAY IMAGING APPARATUS AND METHOD FOR CONTROLLING X-RAY IMAGING APPARATUS

(71) Applicant: SAMSUNG ELECTRONICS CO., LTD., Suwon-si (KR)

(72) Inventors: Dong Goo Kang, Suwon-si (KR); Young Hun Sung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 217 days.

(21) Appl. No.: 13/940,465

(22) Filed: Jul. 12, 2013

(65) Prior Publication Data

US 2014/0016750 A1     Jan. 16, 2014

Related U.S. Application Data

(60) Provisional application No. 61/670,738, filed on Jul. 12, 2012.

(30) Foreign Application Priority Data

Dec. 28, 2012   (KR) .................. 10-2012-0157014

(51) Int. Cl.
*A61B 6/08*      (2006.01)
*H01J 37/304*    (2006.01)
(Continued)

(52) U.S. Cl.
CPC ............ *A61B 6/544* (2013.01); *A61B 6/4476* (2013.01); *A61B 6/469* (2013.01); *A61B 6/547* (2013.01);
(Continued)

(58) Field of Classification Search
CPC .... A61B 6/08; A61B 6/4429; A61B 6/4476; A61B 6/469; A61B 6/467; A61B 6/54; A61B 6/542; A61B 6/544; A61B 6/547; A61B 6/587–6/589; G06T 11/003; G06T 11/005; H01J 37/302; H01J 37/304; H01J 37/3045; G01B 11/00; G01B 11/002; G01B 11/02; G01B 11/022; G01B 11/024; G01B 11/026; G01B 11/14; G01C 3/00; G01C 3/02; G01S 17/02; G01S 17/06; G01S 17/08; G01S 17/46; G01S 17/48
USPC .............. 378/4–20, 62, 63, 91, 95, 98, 98.5, 378/98.8, 145, 162–166, 189, 193, 378/195–198, 204–206, 210, 901; 250/206, 250/206.1, 215, 491.1; 356/3, 4.01, 5.01, 356/20, 29
See application file for complete search history.

(56) References Cited

U.S. PATENT DOCUMENTS 5,457,724 A  * 10/1995  Toth .................................. 378/4
6,155,713 A  * 12/2000  Watanabe ...................... 378/197
(Continued)

FOREIGN PATENT DOCUMENTS

JP         2012-005695 A       1/2012
KR    10-2001-0099718 A      11/2001
(Continued)

*Primary Examiner* — Anastasia Midkiff
(74) *Attorney, Agent, or Firm* — Sughrue Mion, PLLC

(57) ABSTRACT

Disclosed herein are an X-ray imaging apparatus and a method of controlling the same. The X-ray imaging apparatus includes an X-ray emitter to irradiate an object with X-rays and be movable, an X-ray detector to detect X-rays having passed through the object, convert the detected X-rays into an electric signal, and be movable, a location information collector to collect location information regarding the object, and a controller to control the X-ray emitter or the X-ray detector based on the location information regarding the object collected by the location information collector.

20 Claims, 23 Drawing Sheets

(51) Int. Cl.
  *G01C 3/02*     (2006.01)
  *G01S 17/06*    (2006.01)
  *G01B 11/02*    (2006.01)
  *A61B 6/00*     (2006.01)
  *H01J 37/302*   (2006.01)
  *G06T 11/00*    (2006.01)
  *G01N 23/04*    (2006.01)
  *A61B 6/04*     (2006.01)

(52) U.S. Cl.
  CPC ............ *A61B 6/587* (2013.01); *A61B 6/588* (2013.01); *A61B 6/589* (2013.01); *G01B 11/022* (2013.01); *G01B 11/024* (2013.01); *H01J 37/3045* (2013.01); *A61B 6/0492* (2013.01); *A61B 6/08* (2013.01); *A61B 6/4452* (2013.01); *A61B 6/542* (2013.01); *G01B 11/026* (2013.01); *G01C 3/02* (2013.01); *G01N 23/046* (2013.01); *G01N 2223/419* (2013.01); *G01S 17/06* (2013.01); *G06T 11/005* (2013.01); *H01J 37/302* (2013.01); *H01J 37/304* (2013.01)

(56) References Cited

U.S. PATENT DOCUMENTS

| | | | |
|---|---|---|---|
| 6,491,429 B1* | 12/2002 | Suhm | 378/205 |
| 6,611,575 B1* | 8/2003 | Alyassin et al. | 378/37 |
| 7,142,632 B2* | 11/2006 | Atzinger et al. | 378/62 |
| 7,441,953 B2* | 10/2008 | Banks | 378/197 |
| 7,478,949 B2* | 1/2009 | Niessen et al. | 378/205 |
| 2002/0049378 A1* | 4/2002 | Grzeszczuk et al. | 600/427 |
| 2002/0099284 A1* | 7/2002 | Herrmann | 600/407 |
| 2003/0179856 A1* | 9/2003 | Mitschke et al. | 378/205 |
| 2005/0089139 A1* | 4/2005 | Sukovic | 378/20 |
| 2008/0267509 A1* | 10/2008 | Springorum et al. | 382/201 |
| 2009/0262886 A1* | 10/2009 | Mollus et al. | 378/19 |
| 2012/0002790 A1* | 1/2012 | Tanaka | 378/198 |
| 2012/0230563 A1* | 9/2012 | Vik et al. | 382/128 |
| 2013/0163724 A1* | 6/2013 | Marash et al. | 378/91 |
| 2014/0153697 A1* | 6/2014 | Choi et al. | 378/63 |

FOREIGN PATENT DOCUMENTS

| | | |
|---|---|---|
| KR | 10-2008-0064442 A | 7/2008 |
| KR | 10-2009-0078664 A | 7/2009 |
| WO | 00/24333 A1 | 5/2000 |

* cited by examiner

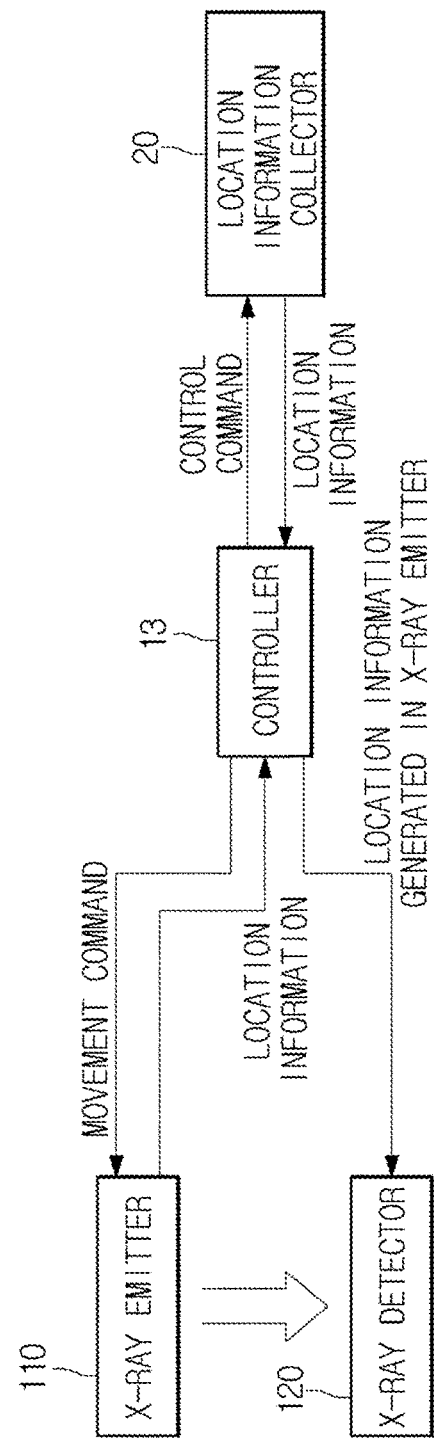

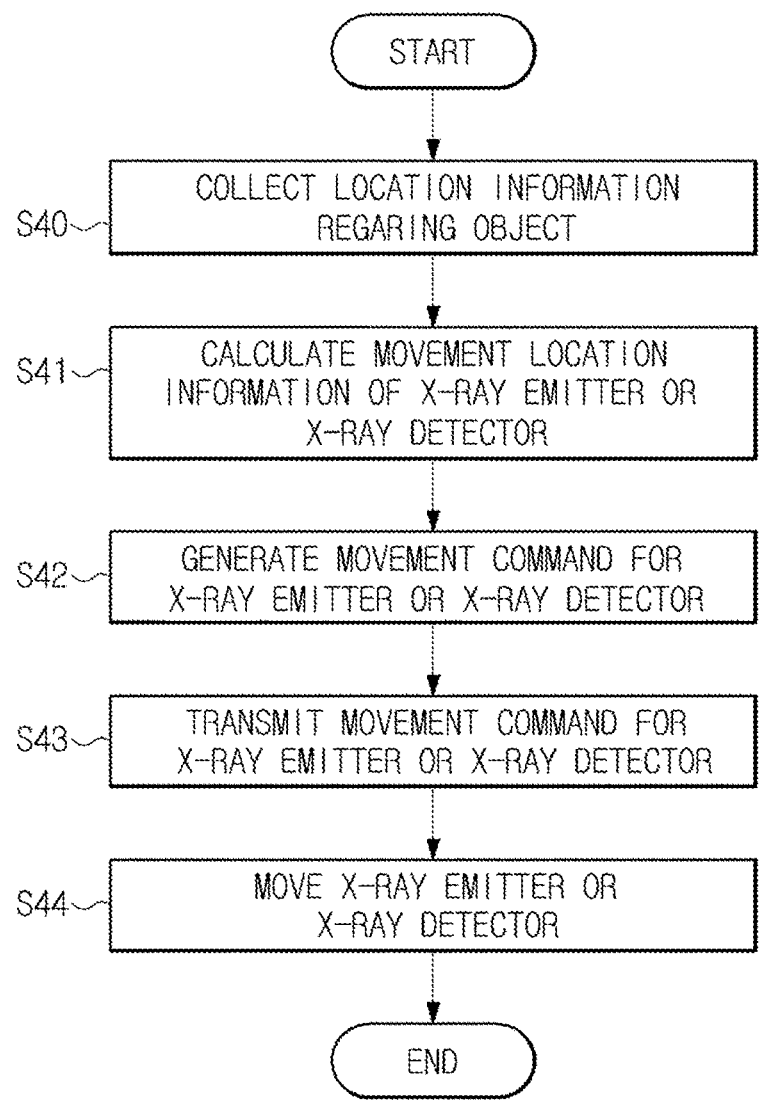

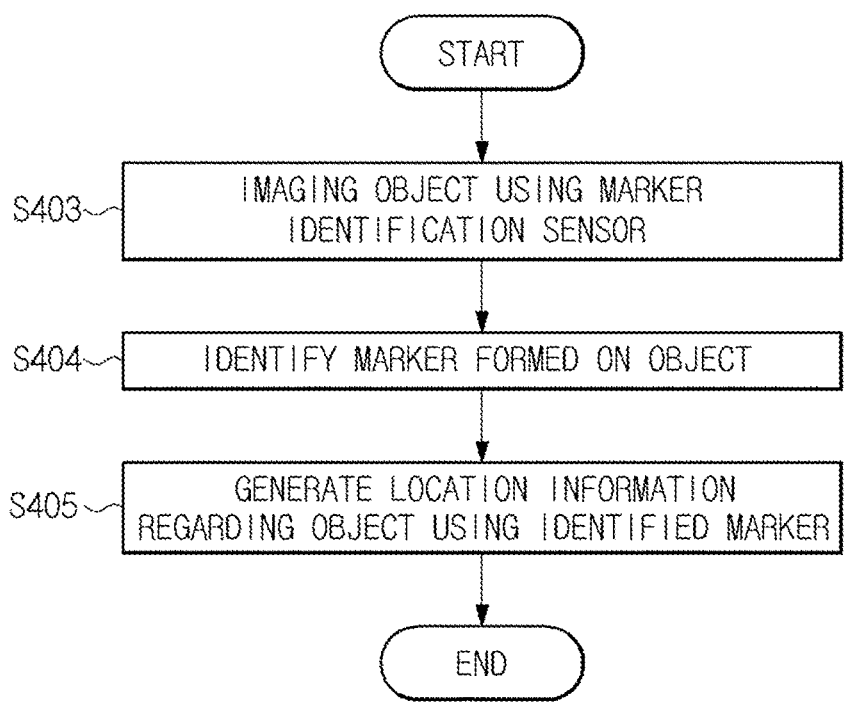

X-RAY IMAGING APPARATUS AND METHOD FOR CONTROLLING X-RAY IMAGING APPARATUS

CROSS-REFERENCE TO RELATED APPLICATION(S)

This application claims the benefit of U.S. Patent Application No. 61/670,738, filed on Jul. 12, 2012, and Korean Patent Application No. 2012-0157014, filed on Dec. 28, 2012 in the Korean Intellectual Property Office, the disclosure of which is incorporated herein by reference.

BACKGROUND

1. Field

Exemplary embodiments relate to an X-ray imaging apparatus and a method of controlling the X-ray imaging apparatus.

2. Description of the Related Art

X-ray imaging apparatuses are imaging systems that acquire an image of the inside of an object by irradiating an object such as a human body, luggage, or the like with X-rays (also referred to as Roentgen rays) to detect tissues, structures or matter inside the object such as a human body, luggage, or the like, and are apparatuses enabling a user, e.g., a doctor or a diagnostician to visually confirm tissues, structures and matter inside an object.

An X-ray imaging apparatus uses, when an object is irradiated with X-rays, absorption or transmission characteristics according to properties of matter on which the X-rays are incident, e.g., density or the like.

In particular, an operating principle of a general X-ray imaging apparatus will be described. An object such as a human body is irradiated with X-rays, X-rays having passed through the object are received, the received X-rays are converted into an electric signal, and an X-ray image is read out from the generated electric signal, thereby generating an X-ray image. The generated X-ray image includes tissues, structures or matter inside the object.

Therefore, the X-ray imaging apparatus may be used to detect abnormalities such as lesions inside the human body, to confirm an inner structure of an object or a component, or to scan luggage at an airport or the like.

Examples of the X-ray imaging apparatus include a digital radiography (DR) apparatus, a computed tomography (CT) apparatus, a full field digital mammography (FFDM) apparatus, and the like.

SUMMARY

Therefore, it is an aspect of the exemplary embodiments to provide an X-ray imaging apparatus and a method of controlling the X-ray imaging apparatus in which a movement location(s) of an X-ray emitter (X-ray source) and/or an X-ray detector may be automatically determined according to a location of an object to be X-ray imaged and, accordingly, X-ray imaging may be performed under optimum viewing conditions.

It is another aspect of the exemplary embodiment to provide a method of controlling the X-ray imaging apparatus in which movement of the X-ray emitter and the X-ray detector may be controlled by transmitting movement location information or a control command for movement to a specific position to both the X-ray emitter and the X-ray detector.

Additional aspects of the invention will be set forth in part in the description which follows and, in part, will be obvious from the description, or may be learned by practice of the invention.

In accordance with one aspect of the exemplary embodiment, an X-ray imaging apparatus includes an X-ray emitter to irradiate an object with X-rays and be movable, an X-ray detector to detect X-rays having passed through the object, convert the detected X-rays into an electric signal, and be movable, a location information collector to collect location information of the object, and a controller to control the X-ray emitter or the X-ray detector based on the location information of the object collected by the location information collector.

The location information collector may be a 3D sensor to sense the object. In addition, the location information collector may be a marker identification sensor to identify a marker attached to the object or installed at the object to collect location information regarding the object.

More particularly, the location information collector may be at least one of a range sensor, a 3D camera, a 3D depth camera, a 3D color/depth camera, a stereo camera, an infrared camera, and a position sensitive device (PSD) sensor.

The X-ray imaging apparatus may further include an input unit through which data or a command is input by a user. Through the input unit may be input user input information including a radiographic location and a radiographic range of the object to be X-ray imaged by a user, unique information of the object, information on a marker to be identified, various setting information needed for operation of the X-ray imaging apparatus or the location information collector, and location information of the object.

In accordance with another aspect of the exemplary embodiment, a method of controlling an X-ray imaging apparatus includes collecting location information on an object, the collecting being performed by a location information collector, determining a movement location of an X-ray emitter or an X-ray detector based on the location information of the object collected by the location information collector, and moving the X-ray emitter or the X-ray detector according to the determined movement location. In this regard, the location information collector may be a 3D sensor to sense the object or a marker identification sensor to identify a marker formed on the object.

BRIEF DESCRIPTION OF THE DRAWINGS

These and/or other aspects of the invention will become apparent and more readily appreciated from the following description of the embodiments, taken in conjunction with the accompanying drawings of which:

FIG. 14 is a block diagram illustrating a structure of an X-ray imaging apparatus according to another exemplary embodiment; and FIGS. 15 through 17 are flowcharts illustrating methods of controlling the X-ray imaging apparatus, according to exemplary embodiments.

DETAILED DESCRIPTION OF THE EXEMPLARY EMBODIMENTS

Figure 1:
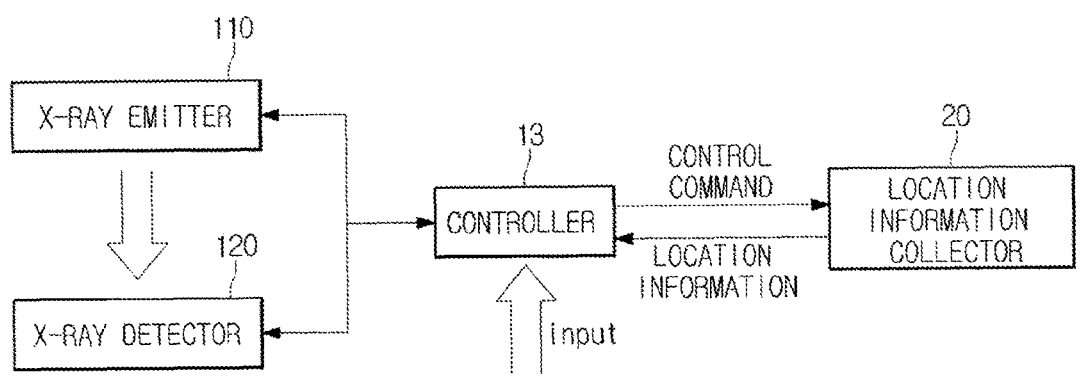
FIG. 1 is a schematic block diagram of an X-ray imaging apparatus according to an exemplary embodiment.

Reference will now be made in detail to the exemplary embodiments, examples of which are illustrated in the accompanying drawings, wherein like reference numerals refer to like elements throughout.

FIG. 1 is a schematic block diagram of an X-ray imaging apparatus according to an exemplary embodiment.

As illustrated in FIG. 1, in the X-ray imaging apparatus 10, an X-ray emitter 110 and an X-ray detector 120 are controlled according to location information collected by a location information collector 20.

In particular, the X-ray imaging apparatus 10 includes the X-ray emitter 110, the X-ray detector 120, and the location information collector 20, and may further include a controller 13 to control the above-listed elements. In the X-ray imaging apparatus 10, the location information collector 20 locates an object and collects information on a location of the object, and the X-ray emitter 110 and the X-ray detector 120 are transferred to a predetermined position to appropriately acquire an X-ray image of the object using the collected location information.

Figure 2:
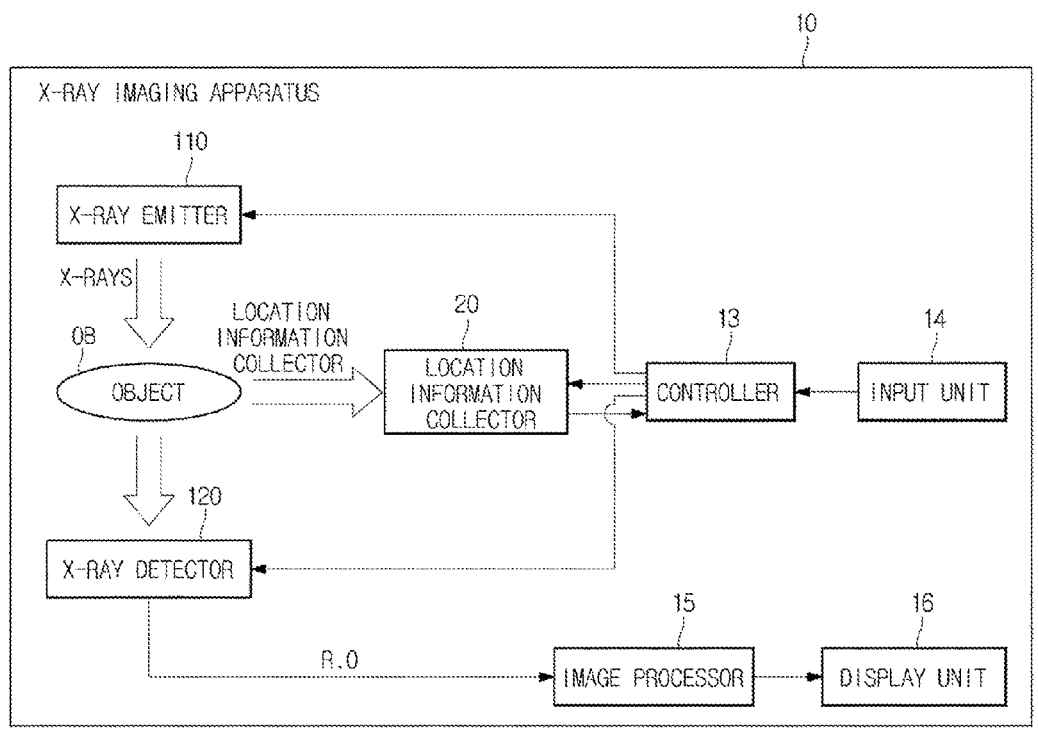
FIG. 2 is a block diagram specifically illustrating a structure of the X-ray imaging apparatus according to the exemplary embodiment.

FIG. 2 is a block diagram specifically illustrating a structure of the X-ray imaging apparatus 10 according to the exemplary embodiment.

As illustrated in FIG. 2, in particular, the X-ray imaging apparatus 10 may include the X-ray emitter 110 to irradiate an object ob with X-rays, the X-ray detector 120 to receive the X-rays radiated from X-ray emitter 110 and convert the received X-rays into an electric signal, the location information collector 20 to collect information on a current location of the object ob, and the controller 13 to control the X-ray emitter 110 and the X-ray detector 120 according to the location information of the object transmitted from the location information collector 20. In this regard, the X-ray emitter 110 and the X-ray detector 120 may be movable to a predetermined position and irradiate the object ob with X-rays or receive the radiated X-rays at the predetermined position.

According to an exemplary embodiment of the X-ray imaging apparatus 10, the location information collector 20 may collect location information regarding the object ob, and the collected location information may be directly transmitted to the X-ray emitter 110 or the X-ray detector 120, or may be transmitted to the X-ray emitter 110 or the X-ray detector 120 via the controller 13.

Alternatively, the controller 13 may receive location information collected by the location information collector 20, generate a control command to control movement of the X-ray emitter 110 and the X-ray detector 120 based on the collected location information, and then transmit the generated control command to the X-ray emitter 110 or the X-ray detector 120. In some cases, the controller 13 may further receive predetermined data or commands from a user and transmit the received predetermined data or commands to the X-ray emitter 110 and the X-ray detector 120. In this regard, the controller 13 may generate new data or commands according to the input predetermined data or commands and then transmit the generated data or commands to the X-ray emitter 110 or the X-ray detector 120.

The X-ray emitter 110 or the X-ray detector 120 is moved to a predetermined position according to the location information or control command transmitted by the controller 13. In this case, the X-ray emitter 110 or the X-ray detector 120 may be moved to an appropriate position to perform X-ray imaging of the object. After movement of the X-ray emitter 110 or the X-ray detector 120 is completed, the X-ray emitter 110 is controlled to irradiate the object with X-rays.

According to an exemplary embodiment, the X-ray imaging apparatus 10 may further include at least one of an input unit 14 to receive a predetermined command from a user, an image processor 15 to generate an X-ray image from the electric signal generated by the X-ray detector 120, and a display unit 16 to display the X-ray image generated by the image processor 15 to a user.

Figure 3A:
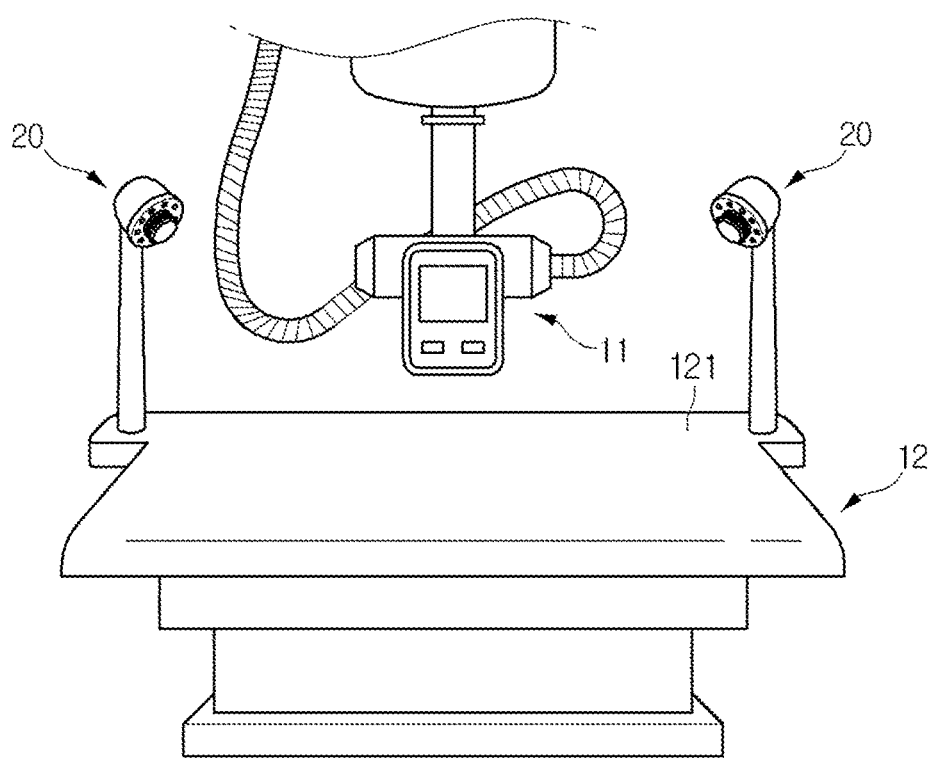
FIGS. 3A and 3B are front views of the X-ray imaging apparatus according to the exemplary embodiment.
Figure 3B:
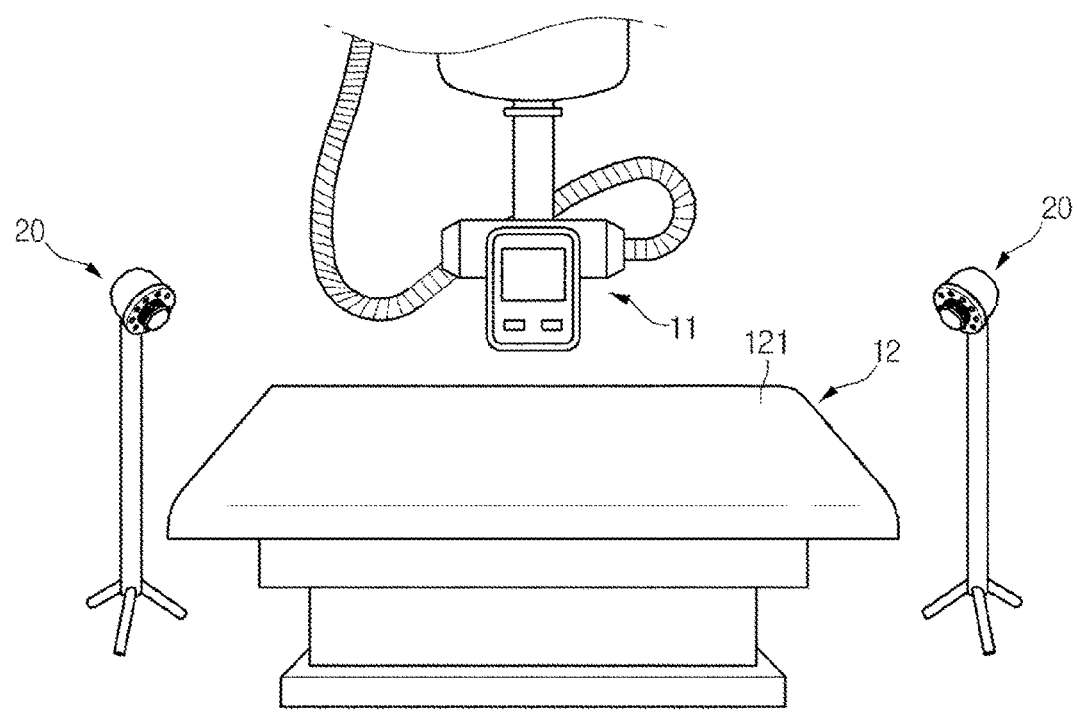

FIGS. 3A and 3B are front views of the X-ray imaging apparatus 10 according to the exemplary embodiment.

As illustrated in FIGS. 3A and 3B, the X-ray imaging apparatus 10 may be, for example, a digital radiation (DR) imaging apparatus. In this exemplary embodiment, the X-ray imaging apparatus 10 includes an X-ray irradiation module 11 that is disposed at an upper part thereof, is movable to a predetermined position, and includes the X-ray emitter 110, and an X-ray detection module 12 that is disposed at a lower part thereof, includes a support table 121 to place an object, detects X-rays radiated from the X-ray irradiation module 11, and has a table shape.

In addition, as illustrated in FIG. 3A, at least one location information collector 20 to collect location information of the object may be installed at a predetermined position of the X-ray imaging apparatus 10, e.g., on an edge portion of the X-ray detection module 12 or at a lower end of the X-ray irradiation module 11. For example, as illustrated in FIG. 3A, 3D sensors or the like may be installed as the location information collector 20. In other alternative embodiments, there may be a sensor instead of the location information collector 20, which determines, calculates or senses the location or position of the object.

As described above, the location information collector 20 may be directly installed at the X-ray irradiation module 11 or the X-ray detection module 12. According to another embodiment, however, as illustrated in FIG. 3B, there is no need to directly install the location information collector 20 at the X-ray irradiation module 11 or the X-ray detection module 12. When, as illustrated in FIG. 3B, the location information collectors 20 are installed to be spaced apart from the X-ray detection module 12, and the location information collectors 20, e.g., a time-of-flight (TOF) camera or the like, collect location information by measuring a distance between an object ob and the location information collector 20 to determine a location of the object ob, however, correction of the distance between the object ob and the location information collector 20 may be further needed.

Hereinafter, a DR imaging apparatus will be described as an example of the X-ray imaging apparatus 10, but exemplary embodiments are not limited thereto. That is, a variety of apparatuses to perform X-ray imaging of an object using other X-rays, such as a computed tomography (CT) apparatus or a full field digital mammography (FFDM) apparatus may be used.

The location information collector 20 collects location information of the object ob mounted on the support table 121 and coverts the location information into a data signal that may be processed by an information processing member, e.g., a processor. The X-ray imaging apparatus 10 determines radiographic position or direction using information collected by the location information collector 20, i.e., a data signal.

The location information collector 20 may be any one of the sensors that sense a location of the object ob, for example, a range sensor, a 3D camera, a 3D depth camera, a 3D color/depth camera, a stereo camera, an infrared camera, a position sensitive device (PSD) sensor, and other devices.

In some cases, the location information collector 20 may include a plurality of sensors to collect accurate location information. In this regard, the sensors may be a set of the same kind of sensors or a set of different kinds of sensors. For example, the location information collector 20 may include at least one range sensor and at least one 3D depth camera to collect location information of the object ob.

Figure 4A:
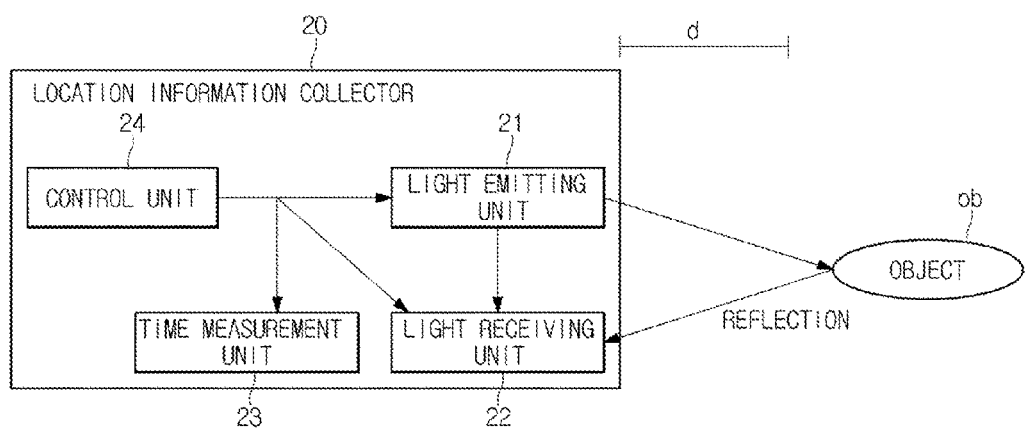
FIGS. 4A and 4B are a block diagram and a view of a location information collector, according to an exemplary embodiment.
Figure 4B:
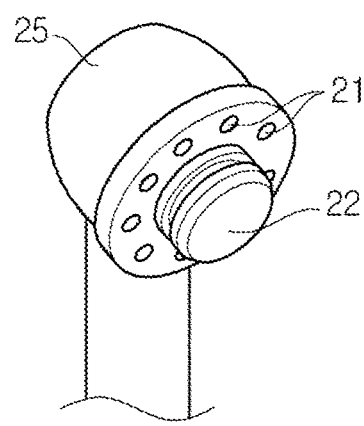

FIGS. 4A and 4B are a block diagram and a view of the location information collector 20, i.e., a TOF camera, which is a 3D depth camera, according to an exemplary embodiment.

The 3D depth camera measures a distance between an object ob and a camera through a camera image to obtain location information of the object ob, e.g., a 3D space coordinate. For example, the 3D depth camera may be a TOF camera.

The TOF camera irradiates the object ob with predetermined light, receives light reflected from the object ob, measures a distance between the TOF camera and the object ob by measuring time elapsing between irradiation and receipt of light, and then acquires location information of the object ob, e.g., a 3D space coordinate of the object ob based on the distance therebetween. That is, the speed of light is known and thus, when time taken for light reflected from the object ob to return is measured, the distance between the TOF camera and the object ob may be measured.

As illustrated in FIGS. 4A and 4B, the location information collector 20, e.g., a TOF camera, may include a light emitting unit 21, a light receiving unit 22, a time measurement unit 23, and a location information collector control unit 24.

The light emitting unit 21 generates predetermined light, e.g., visible light or infrared light and irradiates an object ob with the predetermined light. Thus, the light emitting unit 21 may include a light emitting device that converts electrical energy into light energy, such as a light emitting diode (LED), a laser diode or the like and a power supply to supply electrical energy to the light emitting device. As illustrated in FIG. 4B, a plurality of light emitting units 21 may be disposed at a predetermined position.

The light receiving unit 22 receives light reflected from the object ob after being emitted from the light emitting unit 21. The light receiving unit 22 includes at least one lens to collect light having been reflected and returned to the location information collector 20. In some cases, the light receiving unit 22 may further include an optical filter to filter light so that only some of the reflected light beams pass through the lens.

In this case, the optical filter may transmit only light having a predetermined wavelength or a predetermined energy band. In this regard, the predetermined wavelength or energy band of light passing through the optical filter may be the same as that of predetermined light emitted from the light emitting unit 21. Since the optical filter selectively transmits only light reflected from the object ob among received light beams and blocks other light beams, e.g., light beams transmitted from other light sources, the light receiving unit 22 may receive only the light reflected from the object ob after being emitted from the light emitting unit 21. Therefore, the location information collector 20 may more accurately measure a location of the object ob.

As illustrated in FIG. 4B, the light receiving unit 22 may be disposed in the same direction as the light emitting unit 21 of the location information collector 20 to receive light reflected from the object ob.

The time measurement unit 23 measures round-trip time of light emitted from the light emitting unit 21, reaching the object ob, being reflected from the object ob, and reaching the light receiving unit 22. The time measurement unit 23 may be, for example, an image sensor.

The control unit 24 calculates a distance d between the location information collector 20 and the object ob using the round-trip time of light measured by the time measurement unit 23. In an exemplary embodiment, the control unit 24 may simply calculate the distance d between the location information collector 20 and the object ob by multiplying the speed of light by the round-trip time of light and then dividing the resultant value by 2. Thus, by acquiring information on the distance d between the location information collector 20 and the object ob, the location information collector 20 may acquire the location of the object ob based on the location information collector 20, i.e., location information of the object.

In addition, the control unit 24 may control light emission of the light emitting unit 21 by, if necessary, generating a control command for light emission of the light emitting unit 21 and transmitting the generated control command to the light emitting unit 21, e.g., a power supply of the light emitting unit 21. In addition, the control unit 24 may generate various control commands for the other elements, e.g., the light receiving unit 22 or the time measurement unit 23 to control the elements.

In addition, as illustrated in FIG. 4B, the location information collector 20 may further include a housing 25 equipped with the above-described elements, e.g., the light emitting unit 21, the light receiving unit 22, the time measurement unit 23, and the control unit 24. In this regard, the light emitting unit 21 and the light receiving unit 22 may be installed at the housing 25 to be exposed to the outside as illustrated in FIG. 4B.

Figure 5:
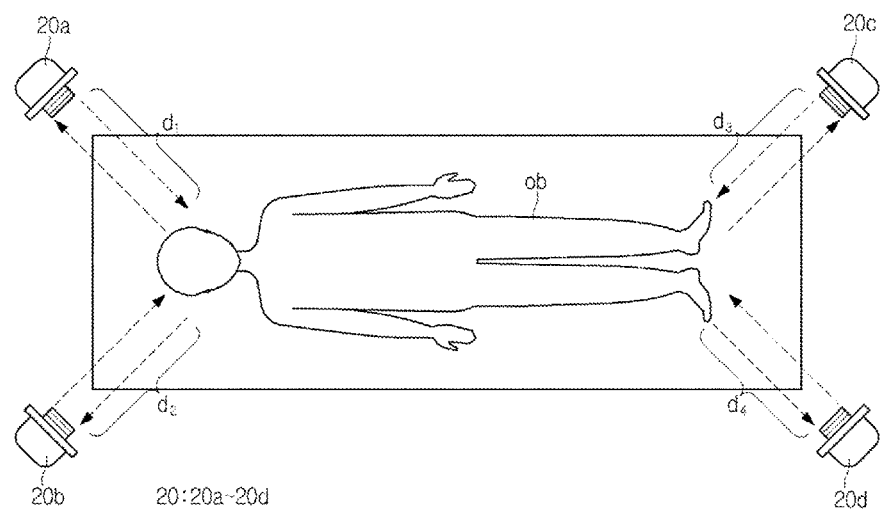
FIG. 5 is a plan view of a location information collector, according to an exemplary embodiment.

FIG. 5 is a plan view of location information collectors 20a, 20b, 20c and 20d, according to an exemplary embodiment.

In this exemplary embodiment, the location information collectors 20a, 20b, 20c and 20d of the X-ray imaging apparatus 10 may be installed at sides of the X-ray detection module 12. As illustrated in FIG. 5, the location information collectors 20a, 20b, 20c and 20d may be respectively installed at four edges or corners of the X-ray detection module 12. According to another exemplary embodiment, although not shown, the location information collectors 20a, 20b, 20c and 20d may be respectively installed at predetermined positions of four sides of the X-ray detection module 12, e.g., at central portions of the four respective sides.

When a plurality of location information collectors is installed in this manner, the location information collectors 20a, 20b, 20c and 20d may acquire distances d1 to d4 between the object ob and each of the location information collectors 20a, 20b, 20c and 20d at each position. Therefore, the X-ray imaging apparatus 10 may acquire accurate location information on the object ob.

In addition, the location information collector 20 may be installed at the X-ray irradiation module 11. In this case, the location information collector 20, e.g., a TOF camera may irradiate an object with predetermined light downward, receive light reflected from the object ob, and calculate a distance between the location information collector 20 and the object ob based on the received light to acquire location information of the object ob, e.g., coordinates of the object with respect to a vertical axis, i.e., z axis.

According to another exemplary embodiment, the X-ray imaging apparatus 10 may collect location information using a marker formed on the object ob using a method such as attachment.

Figure 6:
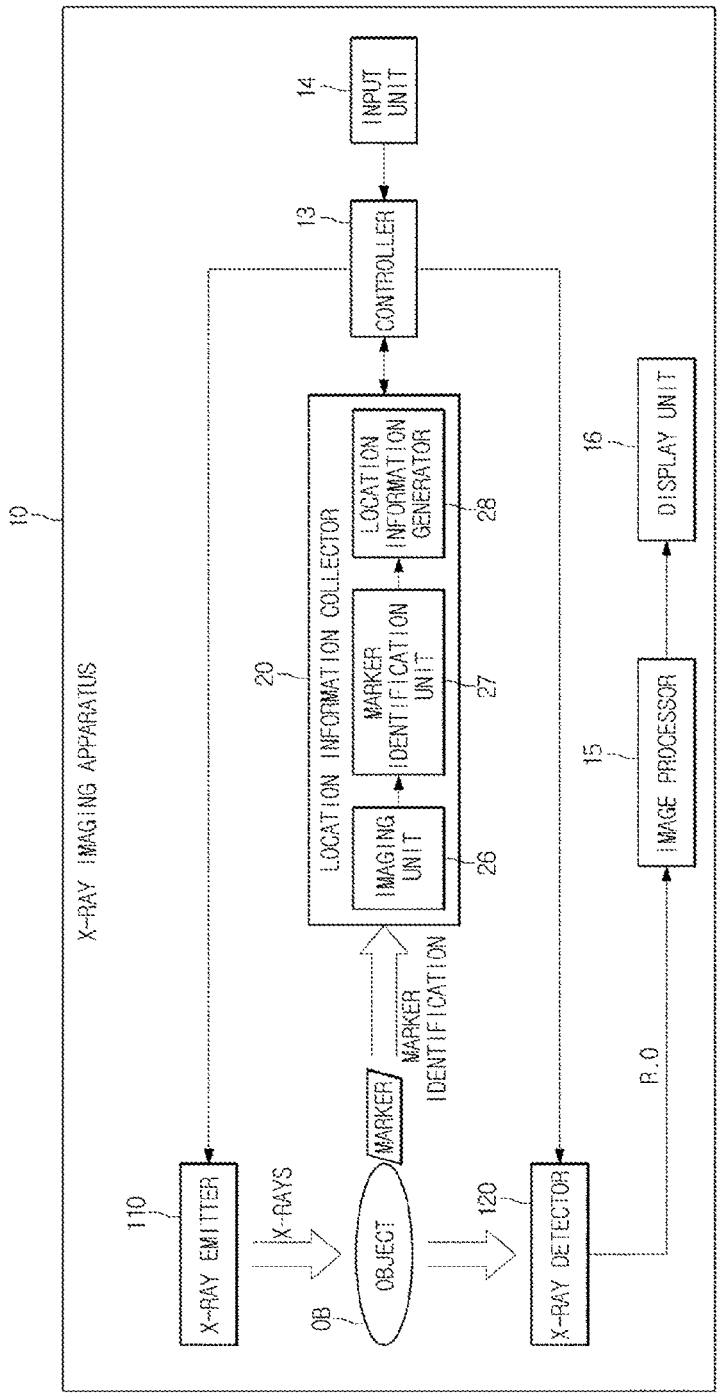
FIG. 6 is a block diagram illustrating a structure of an X-ray imaging apparatus according to another exemplary embodiment.
Figure 7:
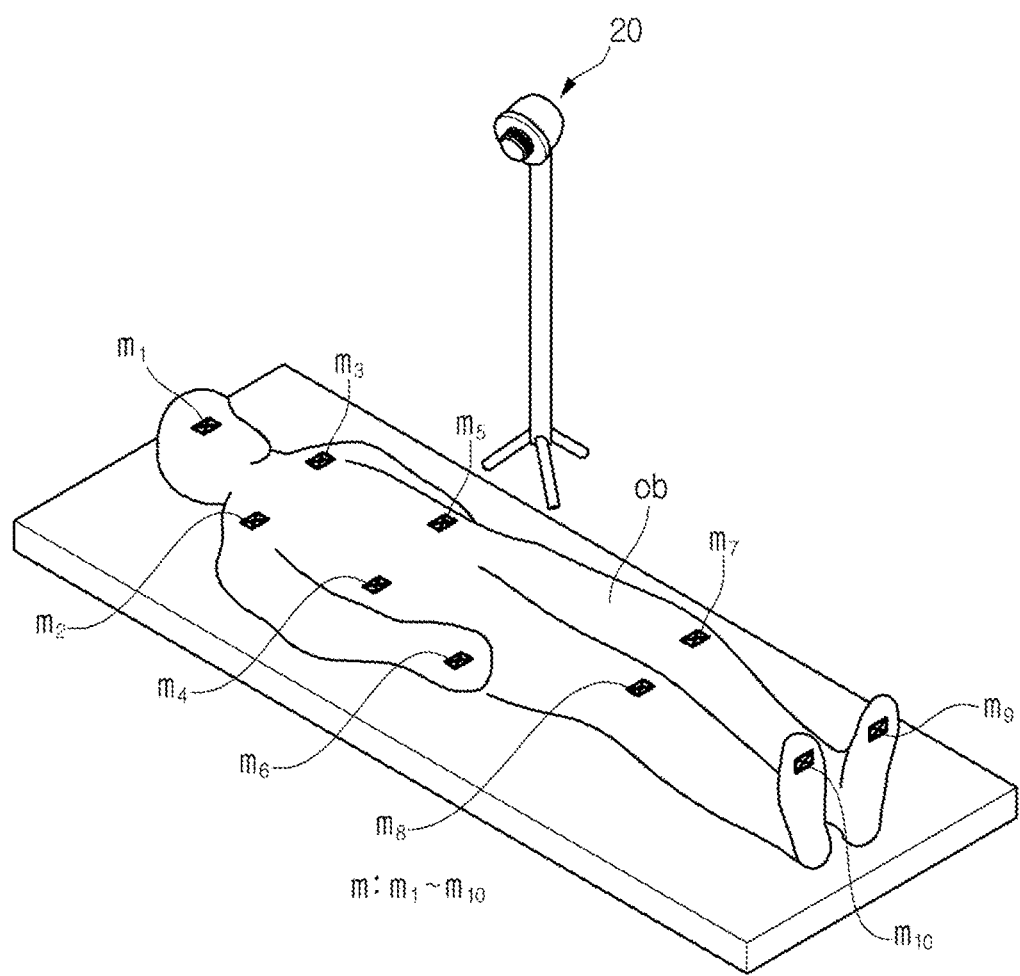
FIG. 7 is a view of a case in which a marker is attached to an object, according to an exemplary embodiment.

FIG. 6 is a block diagram illustrating a structure of an X-ray imaging apparatus 10 according to another exemplary embodiment. FIG. 7 is a view of a case in which a marker is attached to an object, according to an exemplary embodiment.

As illustrated in FIG. 7, a location information collector 20 may be a marker sensor that senses markers m1 to m10 formed on the object ob using a method such as attachment, installation, or coupling to collect location information of the object ob.

The markers m1 to m10 may be used as a target that may be separately identified from the surrounding other objects, for example, the object ob. As illustrated in FIG. 7, the markers m1 to m10 may be partially or entirely attached to or coupled with the object ob by an adhesive material or a coupling member. For example, the markers m1 to m10 may be adhesive patches or the like.

The markers m1 to m10 may be identified after being imaged by the location information collector 20 of the X-ray imaging apparatus 10. Thus, to be distinguishable from the surrounding objects, e.g., the object ob, the markers m1 to m10 may have a color distinctly distinguishable from the object ob, e.g., a color that is complementary to that of the object ob, or may have an image such as a predetermined characteristic pattern on an outer surface thereof, which is formed by printing or the like. The markers m1 to m10 with predetermined characteristic patterns printed thereon may be augmented reality markers (AR markers) used in AR. Alternatively, the markers m1 to m10 may be infrared markers.

In addition, in some exemplary embodiments, each of the markers m1 to m10 may have a unique identification number assigned to distinguish the markers m1 to m10 from one another and may have different colors or different characteristic patterns according to the assigned identification numbers.

The location information collector 20 may include an imaging unit 26, a marker identification unit 27, and a location information generator 28, as illustrated in FIG. 6.

The imaging unit 26 receives visible light or infrared light reflected from the object ob, converts the received visible light or infrared light into an electric signal corresponding thereto, and generates a predetermined image of the object ob based on the generated electric signal. In other words, the imaging unit 26 performs imaging of the object. For example, as illustrated in FIG. 7, the imaging unit 26 performs imaging of the object ob with the markers m1 to m10 attached thereto, e.g., a human body to generate an image of the object ob, e.g., a human body. The imaging unit 26 may be, for example, a general camera. In addition, an infrared camera or the like may be used as the imaging unit 26.

The marker identification unit 27 extracts the marker m from the image generated by the imaging unit 26. For example, when imaging is performed by a camera or the like, the marker identification unit 27 may identify the marker m in the image and extract the marker m to generate, for example, a separate image.

According to an exemplary embodiment, the marker identification unit 27 may identify the marker m by extracting a predetermined color of the marker m from the captured image.

Figure 8A:
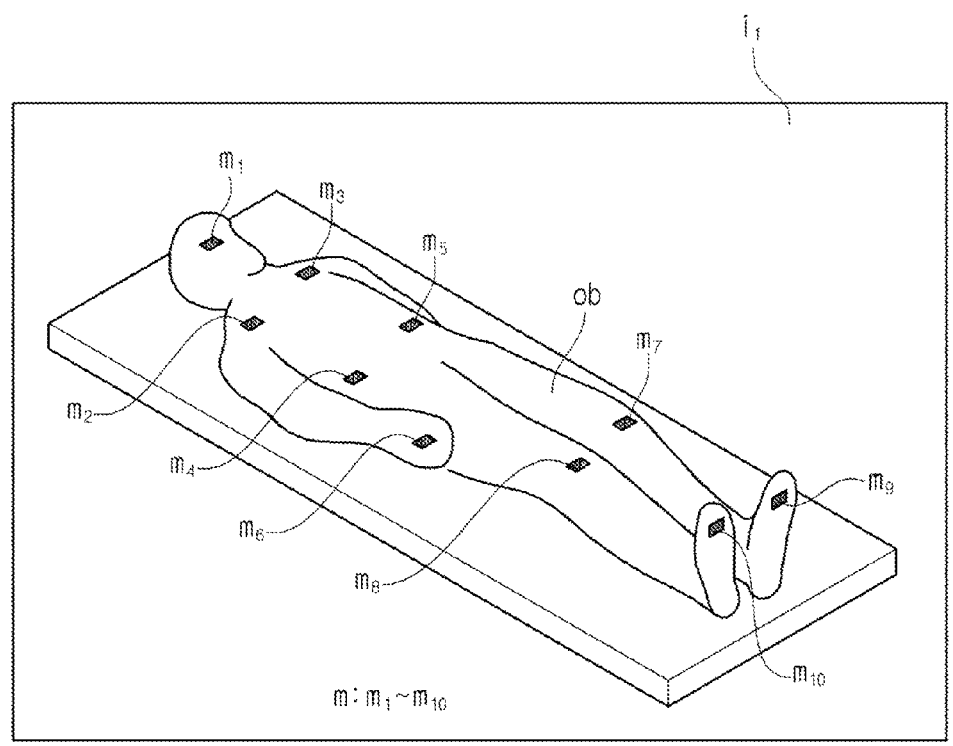
FIGS. 8A and 8B are views for explaining a method of identifying a marker using the X-ray imaging apparatus, according to an exemplary embodiment.
Figure 8B:
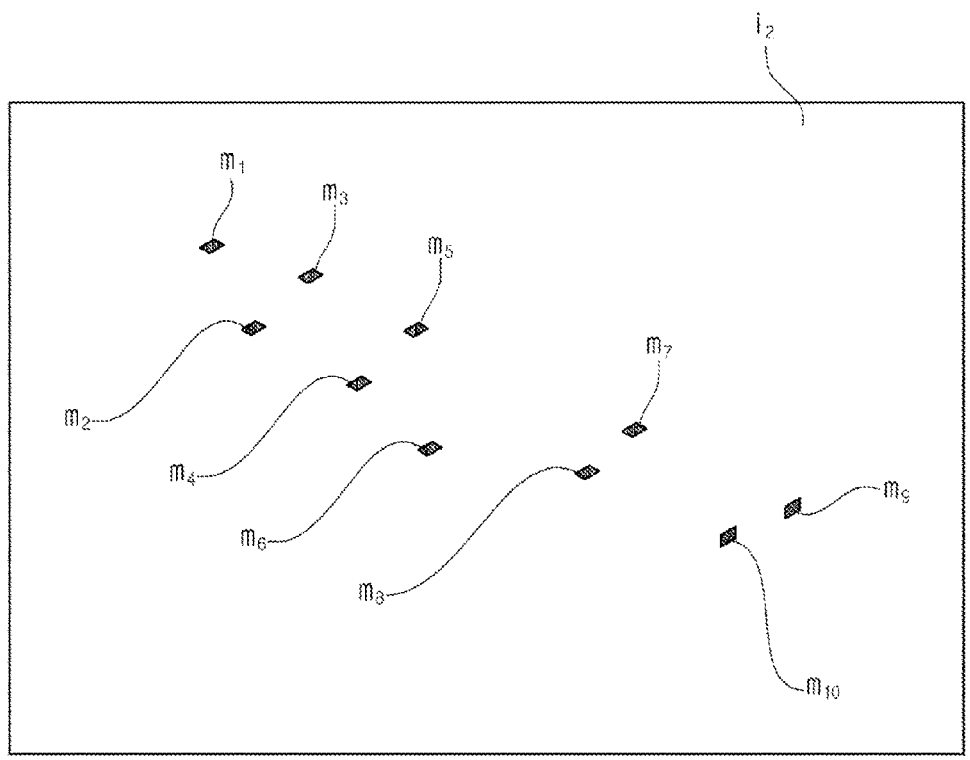

FIGS. 8A and 8B are views for explaining a marker identification method according to an exemplary embodiment.

As illustrated in FIG. 8A, the markers m1 to m10 may have a color distinguishable from the object ob, e.g., a color distinguishable from a color of a patient gown when the object ob is a human body wearing a patient gown, e.g., blue or white. For example, the markers m1 to m10 may be red, or the like.

Then, as illustrated in FIG. 8B, the marker identification unit 27 identifies the markers m1 to m10 by extracting the color (i.e., red) of the markers m1 to m10 from a captured image i1 illustrated in FIG. 8A.

According to another exemplary embodiment, the marker identification unit 27 may identify the marker m by extracting a predetermined characteristic pattern from a captured image.

Figure 9A:
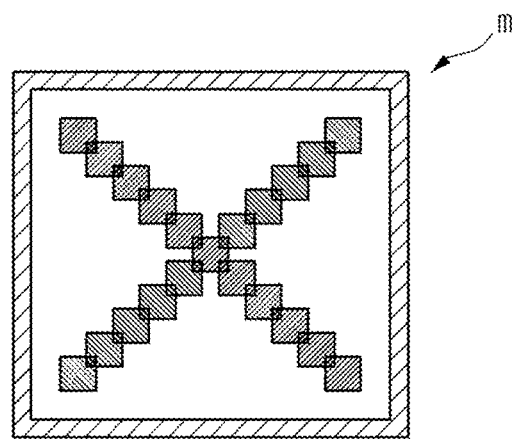
FIGS. 9A through 9C are views for explaining a method of identifying a marker using the X-ray imaging apparatus, according to another exemplary embodiment.
Figure 9B:
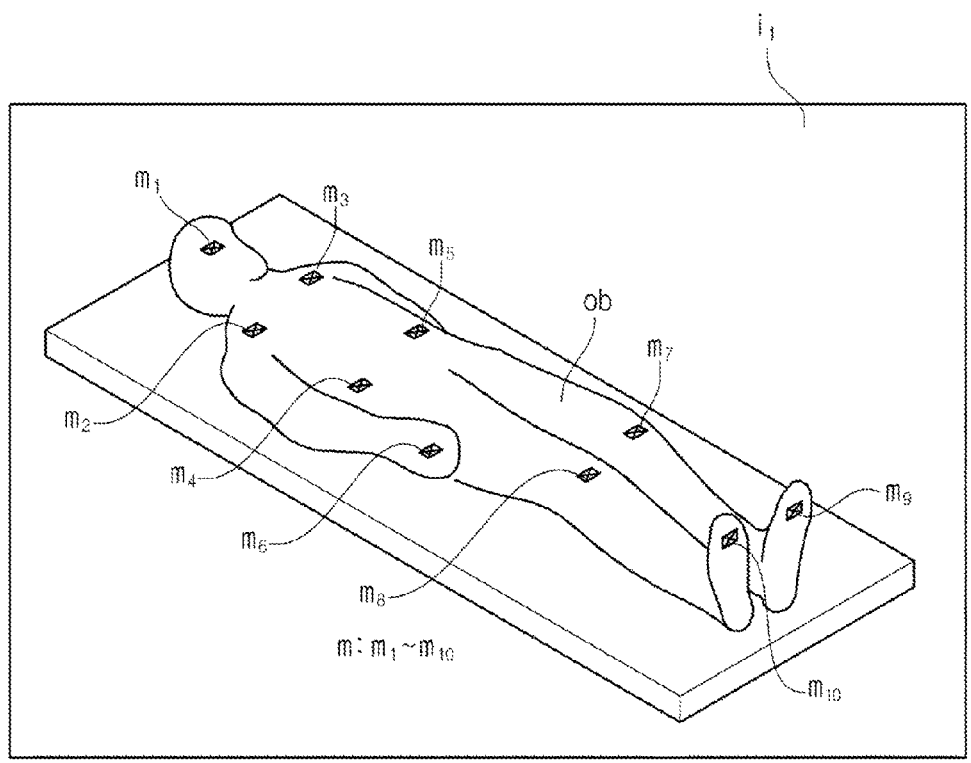
Figure 9C:
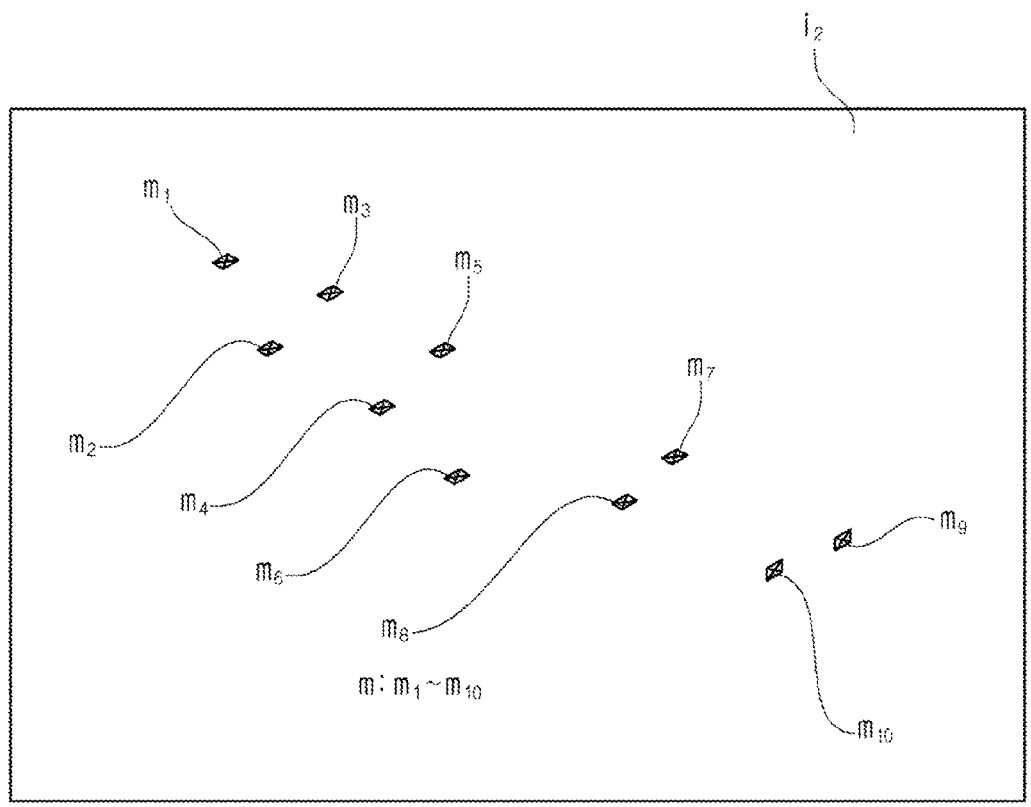

FIGS. 9A through 9C are views for explaining a marker identification method according to another exemplary embodiment.

In an exemplary embodiment, a predetermined characteristic pattern may be formed on markers m1 to m10 using a method such as printing. For example, the characteristic pattern may be a predetermined figure or consist of a combination of a plurality of figures. As an example, the characteristic pattern may consist of a combination of a tetragon and letter 'X' as illustrated in FIG. 9A.

The marker identification unit 27 searches for the characteristic pattern as illustrated in FIG. 9A from an image i1 captured by the imaging unit 26, as illustrated in FIG. 9B. According to search results, the markers m1 to m10 attached to an object ob are distinguished from other objects, e.g., the object ob, to extract the markers m1 to m10 as illustrated in FIG. 9C.

In such manner, the markers m1 to m10 attached to the object ob, e.g., a human body may be identified by the marker identification unit 27 and, consequently, the X-ray imaging apparatus 10 may identify the object ob mounted on the support table 121 of the X-ray detection module 12.

In an exemplary embodiment, the marker identification unit 27 may identify infrared markers m1 to m10.

In addition, the marker identification unit 27 may distinguish the markers m1 to m10 from one another using different colors or different characteristic patterns on the markers m1 to m10. For example, when a characteristic pattern of a marker m attached to the heart consists of the combination of a square and letter 'X' as illustrated in FIG. 9A and differs from characteristic patterns of other markers m, the marker identification unit 27 may further identify the marker m attached to the heart.

The location information generator 28 of the location information collector 20 generates location information of the object ob using the extracted marker m. For example, the location information generator 28 may calculate a location (e.g., a three-dimensional coordinate) of the object ob based on a location of the extracted marker m.

For example, the location information generator 28 may measure the location of the object ob based on the location information collector 20 by calculating how much the marker m is distanced from the location information collector 20, i.e., a distance between the marker m and the location information collector 20, based on size of the extracted marker m, e.g., size of the characteristic pattern printed on the marker m.

In addition, the location information generator 28 may identify a unique identification number assigned to each of the markers m1 to m10 using different colors or characteristic patterns of the respective markers m1 to m10 and detect a direction in which the object ob, e.g., an human body lies or a location of each of the organs inside the human body according to the unique identification numbers. As described above, the location information generator 28 may further measure separately only a location of the heart using a marker m attached to the heart.

Moreover, the location information generator 28 may calculate an actual direction in which the marker m is disposed based on a location of the marker m extracted in a captured image, and may also measure a location of each of the markers m1 to m10 based on calculation results.

Furthermore, the location information generator 28 may calculate a size of the object ob, e.g., a human body using the markers m1 to m10 extracted, and may also calculate a central portion of the object ob to some extent using the markers m1 to m10.

Thus, the location information collector 20 may acquire various information on the object ob or a part of the object ob, in particular, location information on the object ob or a part of the object ob, using at least one of the markers m1 to m10. In this case, the location information of the object ob may be, for example, a three-dimensional coordinate for the object ob.

The X-ray imaging apparatus 10 may include the X-ray irradiation module 11 as illustrated in FIGS. 3A and 3B.

Figure 10:
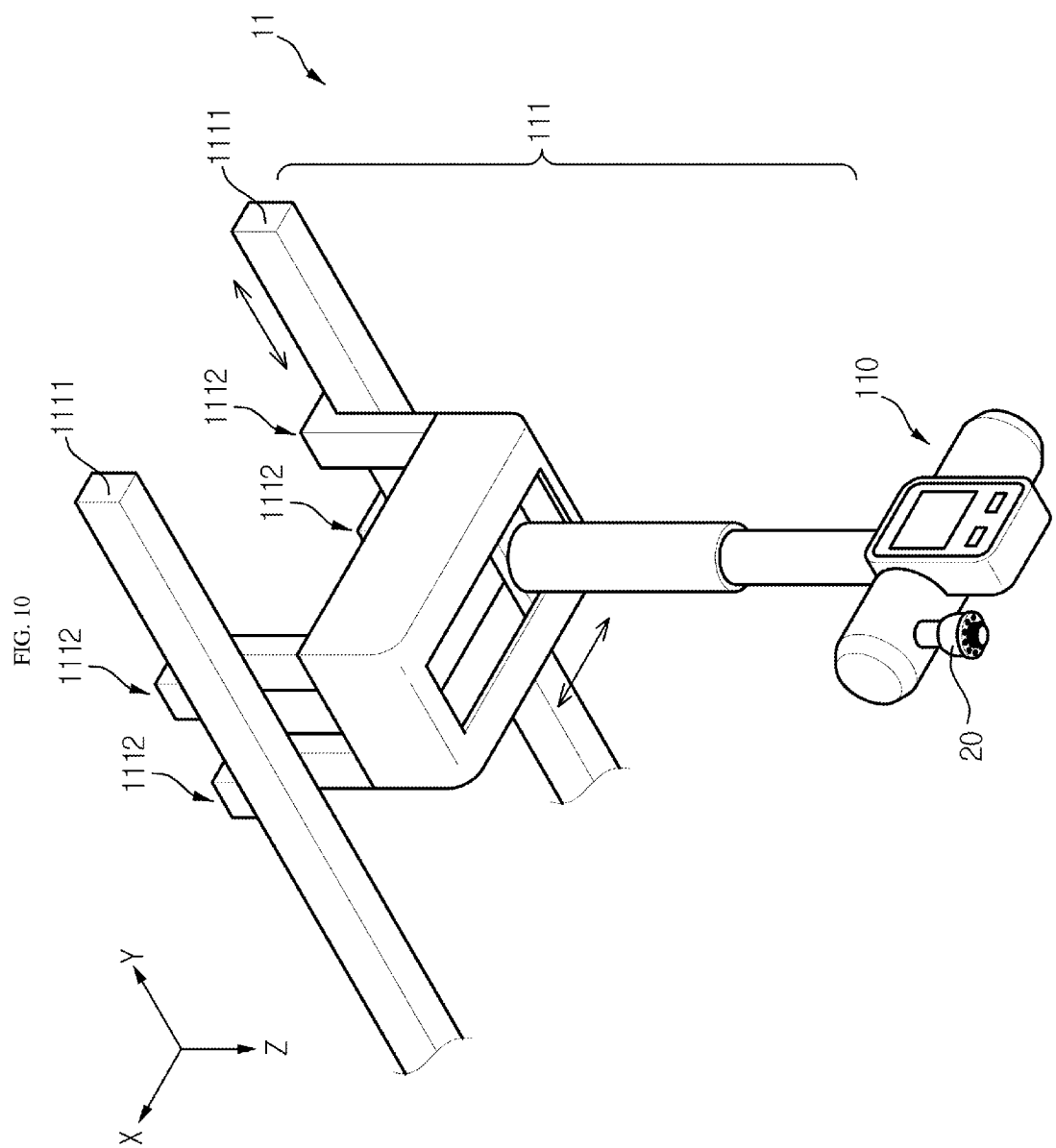
FIG. 10 is a perspective view of an X-ray irradiation module, according to an exemplary embodiment.

FIG. 10 is a perspective view of the X-ray irradiation module 11 of the X-ray imaging apparatus 10. The X-ray irradiation module 11 is movable so as to irradiate an object ob with X-rays at a plurality of positions. In particular, as illustrated in FIG. 10, the X-ray irradiation module 11 may further include a moving part 111. The moving part 111 may include, for example, rails 1111 and connection parts 1112 moving along the rails 1111. The connection parts 1112 may include, for example, wheels that contact the rails 1111 to be driven along the rails 1111. When the connection parts 1112 run along the rails 1111, other elements of the X-ray irradiation module 11 connected to the rails 1111 via the connection parts 1112, e.g., the X-ray emitter 110 and the like are transferred to a predetermined position according to movement of the connection parts 1112. That is, the X-ray emitter 110 is movable along the rails 1111. As illustrated in FIG. 10, the rails 1111 are installed in parallel above the X-ray irradiation module 11 so that other elements of the X-ray irradiation module 11 may be movable in at least one direction, e.g., a Y-axis direction. Alternatively, a plurality of rails may be installed in a plurality of directions so that the X-ray emitter 110 is movable in various directions, e.g., X and Y-axis directions. The X-ray irradiation module 11 may include, for example, a robot arm instead of the rails 1111. The X-ray emitter 110 may be installed such that it is connected to a robot arm and thus movable to a predetermined position according to operation of the robot arm. In addition, the X-ray irradiation module 11 may be configured such that the X-ray emitter 110 is movable to a predetermined position according to operation of a pneumatic cylinder or a hydraulic cylinder connected to the X-ray emitter 110. In addition, other members that transfer an element to a certain position may also be applied to the X-ray irradiation module 11 within the scope of the present invention.

According to an exemplary embodiment, the location information collector 20 may be installed at a lower end of the X-ray irradiation module 11. The location information collector 20 has been already described above.

The X-ray irradiation module 11 may be provided at a lower end thereof with the X-ray emitter 110 that irradiates an object with X-rays.

Figure 11:
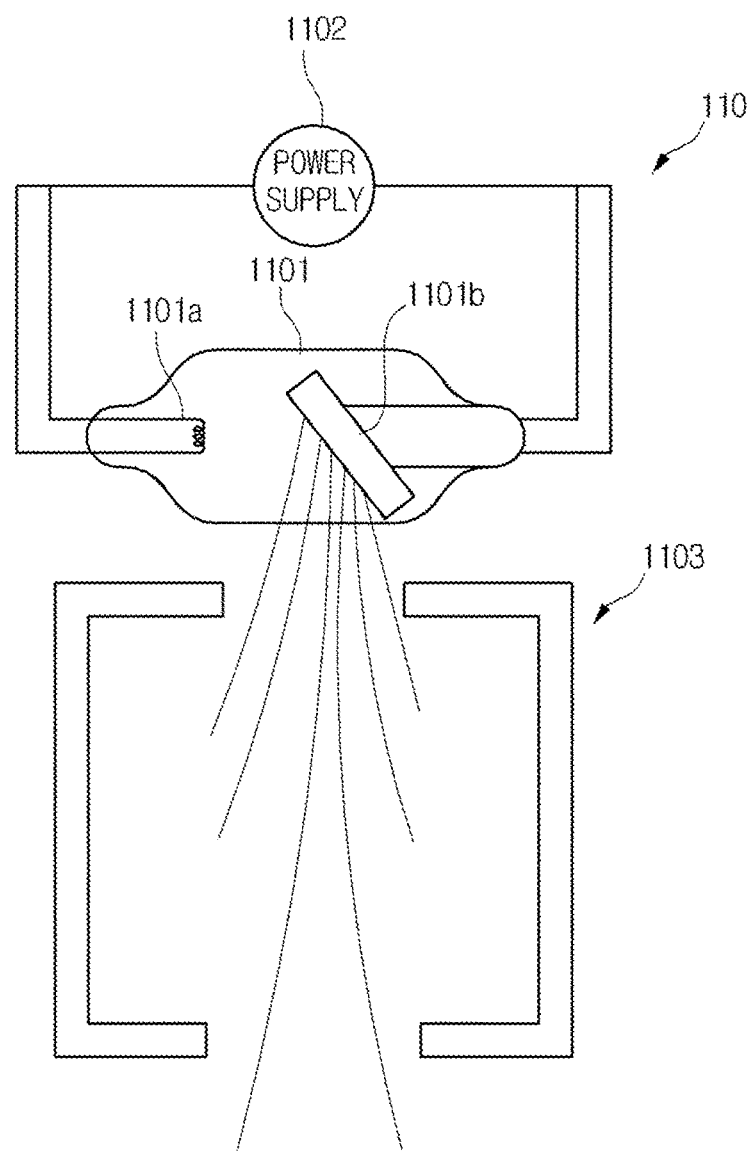
FIG. 11 is a view of an X-ray emitter, according to an exemplary embodiment.

FIG. 11 is a view of the X-ray emitter 110, according to an exemplary embodiment. As illustrated in FIG. 11, the X-ray emitter 110 includes an X-ray tube 1101 to generate X-rays having an energy level corresponding to applied voltage and a power supply 1102 electrically connected to the X-ray tube 1101 to apply a predetermined voltage to the X-ray tube 1101. When a predetermined voltage is applied to the X-ray tube 1101 from the power supply 1102, electrons of a filament 1101a of a cathode inside the X-ray tube 1101 are accelerated and move towards an anode 1101b according to the applied voltage. When the accelerated electrons are rapidly decelerated in the anode 1101b, X-rays are generated from the anode 1101b. The generated X-rays are radiated in a predetermined direction. The generated and radiated X-rays may pass through a collimator 1103, as illustrated in FIG. 11. The collimator 1103 controls an irradiation direction or irradiation range of X-rays by transmitting X-rays that proceed in a direction desired by a user and absorbing and filtering X-rays that proceed in other directions.

Referring back to FIGS. 3A and 3B, the X-ray imaging apparatus 10 may include the X-ray detection module 12.

Figure 12:
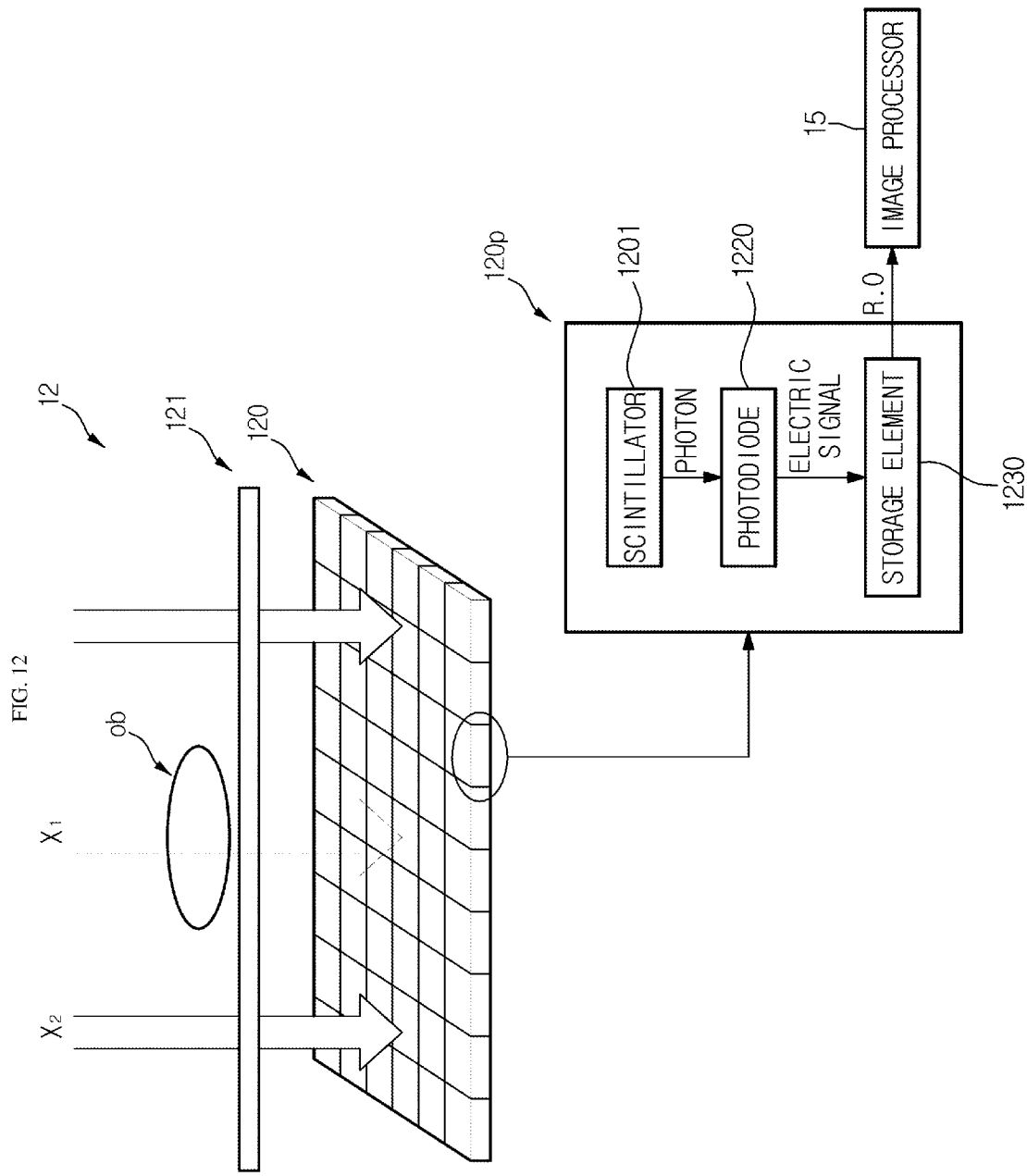
FIG. 12 is a view of an X-ray detection module, according to an exemplary embodiment.

FIG. 12 is a view of the X-ray detection module, according to an exemplary embodiment. The X-ray detection module 12 includes the support table 121 at an upper end thereof to place an object ob and the X-ray detector 120 that receives X-rays X1 having passed through the object ob or X-rays X2 not having passed through the object ob and having directly reaching and is movable. In particular, the X-ray detector 120 may be an X-ray detection panel to detect X-rays. The X-ray detection panel may be divided into a plurality of pixels 120p. Each pixel 120p may include a scintillator 1201 to output visible light photons by receiving and emitting incident X-rays, a photodiode 1220 to receive the output visible light photons and then convert the visible light photons into an electric signal, e.g., analog data, and a storage element 1230 to store the generated electric signal, e.g., a storage capacitor. The X-ray detector 120 may further include a substrate on which the scintillator 1201, the photodiode 1220, and the storage element 1230 are provided. Although not shown, the X-ray detection module 12 may further include a separate collimator disposed between the X-ray detector 120 and the object ob to filter X-rays scattered while passing through the object ob. The collimator may be attached to the X-ray detector 120 and thus moved along with the X-ray detector 120.

Figure 13A:
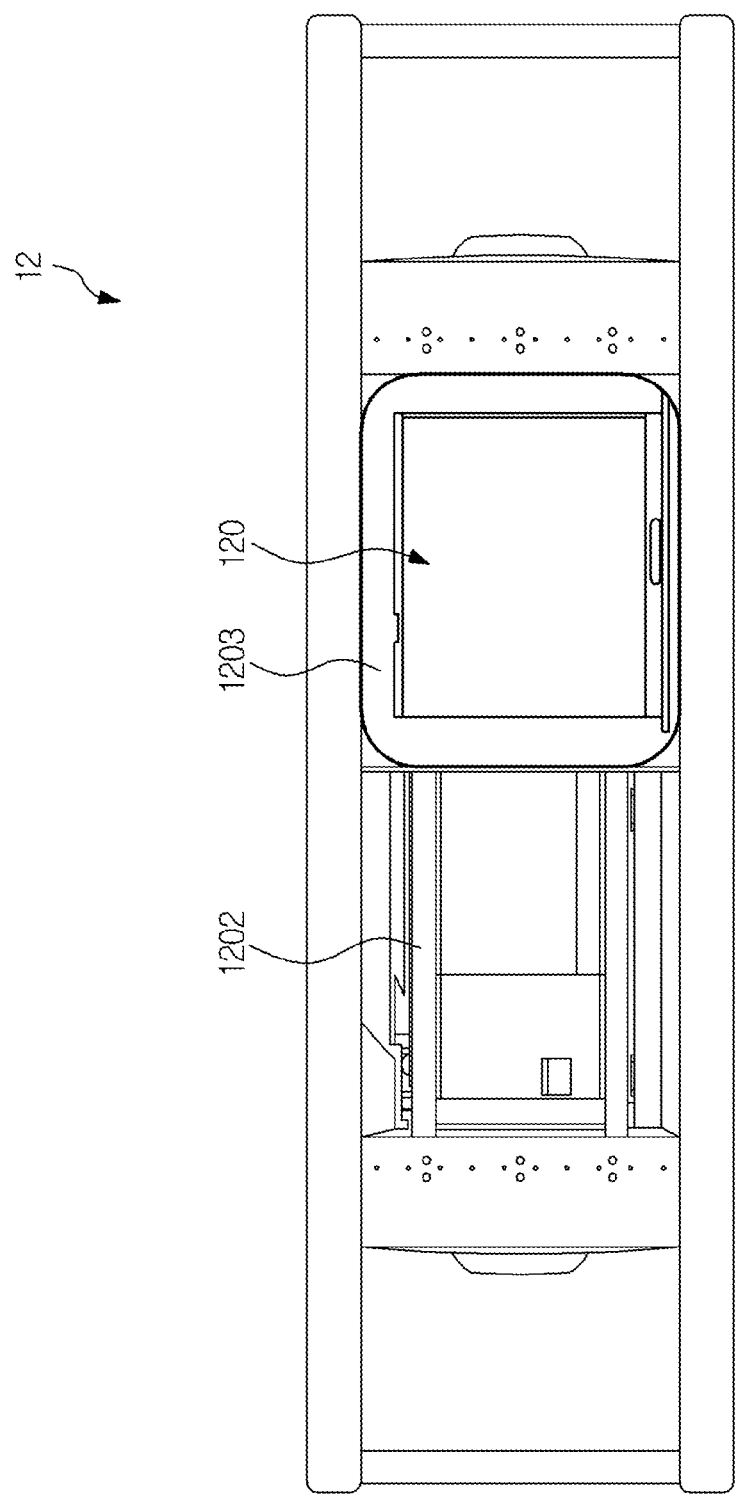
FIGS. 13A and 13B are plan views of X-ray detection modules, according to exemplary embodiments.
Figure 13B:
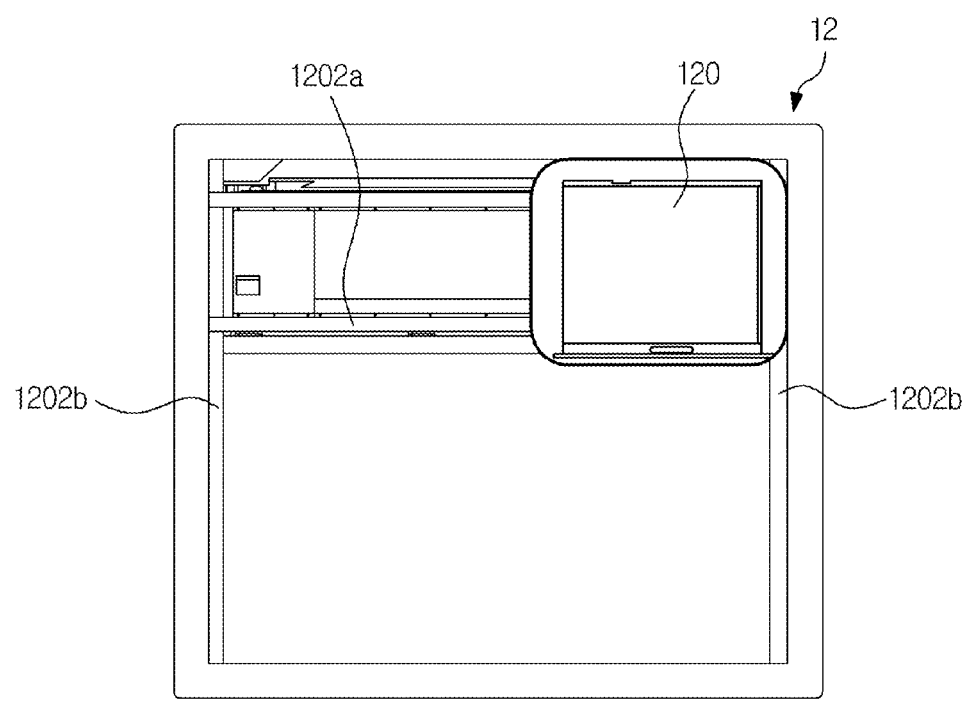

FIGS. 13A and 13B are plan views of the X-ray detection module 12, according to embodiments of the present invention.

As illustrated in FIGS. 13A and 13B, the X-ray detection module 12 may further include rails 1202 to mount the X-ray detector 120 and transfer the X-ray detector 120 to a predetermined position. For example, the X-ray detection module 12 may include a pair of rows of rails 1202 as illustrated in FIG. 13A and may also include a plurality of pairs of rails 1202a and 1202b as illustrated in FIG. 13B. As illustrated in FIG. 13A, when the pair of rows of rails 1202 are installed, the X-ray detector 120 is movable only in one axis direction, e.g., an X-axis direction and, as illustrated in FIG. 13B, when the pairs of rails 1202a and 1202b are installed, the X-ray detector 120 is movable along a plurality of axes, e.g., X-axis and Y-axis directions. That is, in the latter case, the X-ray detector 120 is two-dimensionally moved. An X-ray detector case 1203 is mounted on the rails 1202 or 1202a and 1202b to fix the X-ray detector 120. The X-ray detector case 1203 may be provided at a lower surface thereof or side surfaces thereof with wheels contacting the rails 1202 and driven according to the rails 1202 to stably move the X-ray detector 120 on the rails 1202. Thus, the X-ray detector 120 is movable according to movement of the X-ray detector case 1203 on the rails 1202. According to another embodiment, a robot arm or the like may be used instead of rails to move the X-ray detector 120. According to another exemplary embodiment, the X-ray detector 120 may be moved to a predetermined position according to operation of wheels installed at the X-ray detector case 1203 without rails and may also be moved to a predetermined position according to operation of a pneumatic cylinder or a hydraulic cylinder connected to the X-ray detector 120 or the X-ray detector case 1203. In addition, other members that transfer an element to a certain position may also be used to move the X-ray detector 120 within the scope of the present invention.

Referring back to FIG. 2, the X-ray imaging apparatus 10 may include the controller 13.

The controller 13 controls movement of the X-ray emitter 110 and/or the X-ray detector 120 by generating information on a movement position of the X-ray emitter 110 and/or the X-ray detector 120, i.e., movement location position of the X-ray emitter 110 and/or movement location information of the X-ray detector 120, according to location information of the object ob collected by the location information collector 20 and then transmitting the generated movement location information to the X-ray emitter 110 and/or the X-ray detector 120.

In this case, the controller 13 may calculate optimum movement location information of the X-ray emitter 110 based on the location information of the object ob collected by the location information collector 20 and then calculate movement location information of the X-ray detector 120 optimized to the movement location information of the X-ray emitter 110 using the calculated movement location information of the X-ray emitter 110. In addition, in a reverse manner, movement location information of the X-ray detector 120 may be first calculated.

In addition, if the movement location information of the X-ray emitter 110 is predetermined through a method, such as being input via the input unit 14, which will be described below, the controller 13 may calculate movement location information on an optimum movement location of the X-ray detector 120, e.g., a location enabling the X-ray detector 120 to appropriately receive radiated X-rays, using movement location information of the X-ray emitter 110 separately determined from the location information of the object ob collected by the location information collector 20. In addition, this operation may be implemented in a reverse manner.

If necessary, the controller 13 may generate a movement command for the X-ray emitter 110 and/or the X-ray detector 120 based on the location information of the object ob collected by the location information collector 20 and transmit the generated movement command to the X-ray emitter 110 and/or the X-ray detector 120, to move the X-ray emitter 110 and/or the X-ray detector 120.

The controller 13 may generate movement location information of the X-ray emitter 110 and/or movement location information of the X-ray detector 120, or a movement command for the X-ray emitter 110 and/or a movement command for the X-ray detector 120 according to location information of the object ob so that the X-ray emitter 110 or the X-ray detector 120 performs X-ray imaging of the object ob. Accordingly, X-ray imaging of the object ob may be implemented at an optimum position without unnecessary manual operation by a user.

The controller 13 may be a processor installed at the X-ray irradiation module 11 or the X-ray detection module 12, or a separate information processing apparatus, e.g., a computer device that transmits and receives data to and from the X-ray irradiation module 11 or the X-ray detection module 12 or a processor of the information processing apparatus.

According to an exemplary embodiment, the controller 13 may separately transmit movement location information or movement commands to the X-ray emitter 110 and the X-ray detector 120 as illustrated in FIGS. 1 and 2. That is, the controller 13 may generate movement location information of the X-ray emitter 110 or a movement command therefor based on location information of the object ob through one process and transmit the generated movement location information or movement command to the X-ray emitter 110, and may generate movement location information of the X-ray detector 120 or a movement command therefor based on location information of the object ob through a separate process from the above-described process and transmit the generated movement location information or movement command to the X-ray detector 120.

According to another exemplary embodiment, as illustrated in FIG. 14, the controller 13 may generate only movement location information of any one of the X-ray emitter 110 and the X-ray detector 120 or only a movement command for any one thereof and transmit the generated movement location information or movement command to an element corresponding thereto, i.e., any one of the X-ray emitter 110 and the X-ray detector 120.

In addition, if any one of the X-ray emitter 110 and the X-ray detector 120 is moved according to the transmitted movement location information or movement command, the controller 13 acquires information on location after movement of any one of the X-ray emitter 110 and the X-ray detector 120. Then, the controller 13 may generate movement location information of the other of the X-ray emitter 110 and the X-ray detector 120 or a movement command for the other thereof based on the acquired information on post-movement location of the one thereof and transmit the generated movement location information or movement command to the other of the X-ray emitter 110 and the X-ray detector 120.

In other words, the controller 13 may generate movement location information of both the X-ray emitter 110 and the X-ray detector 120 or commands for movement of both of them and perform controlling such that any one of the X-ray emitter 110 and the X-ray detector 120 is first moved and then the other thereof is moved according to post-movement location of the one thereof.

In addition, the controller 13 may perform controlling of the location information collector 20 by generating a control command for the location information collector 20, e.g., an imaging control command for the imaging unit 26 of the location information collector 20 or a movement command for the location information collector 20 and transmitting the generated control command to the location information collector 20. In this case, the control command for the location information collector 20 may be determined according to input via the input unit 14.

Moreover, the controller 13 may calculate information on movement location of the X-ray emitter 110 or the X-ray detector 120 according to a variety of instructions or commands input via the input unit 14, i.e., user input information.

The X-ray imaging apparatus 10 may further include the input unit 14 through which a predetermined instruction or command is input by a user, as illustrated in FIG. 2.

The input unit 14 may receive predetermined user input information such as a variety of instructions or commands from a user. In this regard, the user input information may include various items to be selected or designated when a user performs X-ray imaging of the object ob, e.g., information on restriction or expansion of an X-ray imaging area such as a radiographic site or a radiographic range (radiographic area) of the object ob to be X-ray imaged by a user, unique information on the object ob, such as a size or volume of the object ob, information on a marker to be identified, various setting information needed to operate the X-ray imaging apparatus 10 or the location information collector 20.

In particular, when a user wishes to perform X-ray imaging on only a specific site of the object ob (e.g., the human body), e.g., the chest part of the human body, the user may input an instruction to designate a specific site of the object ob, location of which is identified, i.e., user input information, via the input unit 14.

In addition, the user input information may include location information of the object ob. In this regard, the location information of the object ob may be location information according to decision of a user, not being collected by the location information collector 20. In addition, the user input information may include information on post-movement location of at least one of the X-ray emitter 110 and the X-ray detector 120. In other words, a user may predetermine a movement location of the X-ray emitter 110 or the X-ray detector 120. In this case, as described above, the controller 13 may calculate movement location information of the X-ray emitter 110 and/or the X-ray detector 120 or generate a movement command therefor using movement location information input by a user and collected location information of the object ob.

When the user input information is input, the controller 13 may calculate information on a movement location of the X-ray emitter 110 and/or the X-ray detector 120 using the user input information input by a user and the location information collected by the location information collector 20. For example, when a user inputs location information on the object ob, the location information collected by the location information collector 20 may be corrected based on the location information input by the user to confirm the location information of the object ob and, accordingly, movement location information of the X-ray emitter 110 and/or the X-ray detector 120 may be generated.

The input unit 14 may be, for example, a joystick, a keyboard, a keypad, a touch screen, a track ball, a mouse, a tablet, or the like. Any one of the above-listed elements may be used as the input unit 14 or the input unit 14 may consist of a combination of at least two thereof. When a tablet is used as the input unit 14, a user may input predetermined information or command by touching the tablet or using a separate tablet pen.

The input unit 14 may be directly installed at the X-ray imaging apparatus 10 or independently installed from the X-ray imaging apparatus 10 and thus transmit instructions, commands, information or the like in a remote manner. When the input unit 14 is separated from the X-ray imaging apparatus 10, the input unit 14 may transmit information or commands input by a user to the controller 13 using a wired communication technology using a wired cable or a wireless communication technology using an electromagnetic wave, a light wave, a sound wave, or ultrasound. In this regard, the wireless communication technology using an electromagnetic wave includes a digital mobile communication technology, and the wireless communication technology using a light wave includes an infrared wireless communication technology that transmits commands or data using infrared light.

The image processor 15 illustrated in FIG. 2 reads out an electric signal stored in the storage element 1230 of the X-ray detector 120 to generate an X-ray image. In addition, if necessary, a 3D image or a live image may be generated by adjusting contrast or brightness of the generated X-ray image or combining generated X-ray images.

The generated X-ray image may be displayed on the display unit 16 to enable a user to view the X-ray image of the object ob at an appropriate position.

Figure 16:
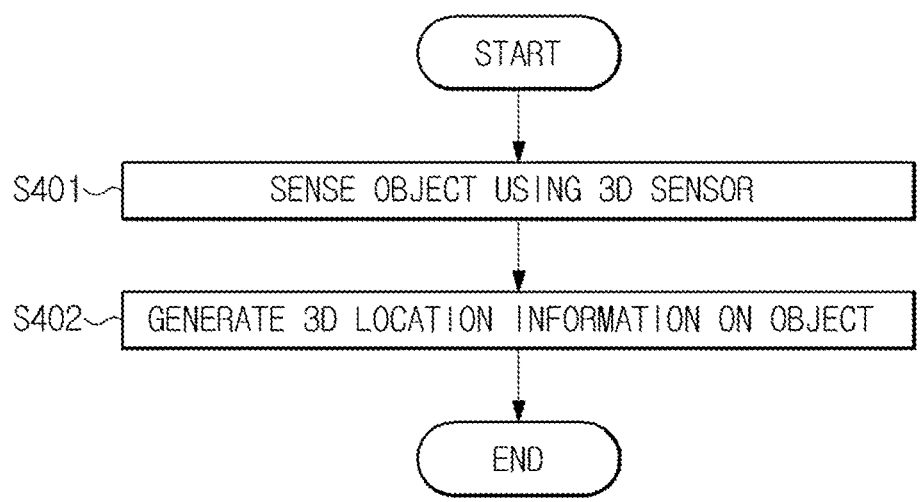

FIGS. 15 through 17 are flowcharts illustrating methods of controlling the X-ray imaging apparatus, according to exemplary embodiments.

As illustrated in FIG. 15, according to the method of controlling the X-ray imaging apparatus 10, first, the location information collector 20 collects location information on the object ob (operation S40). Then, the X-ray imaging apparatus 10 calculates movement location information of at least one of the X-ray emitter 110 and the X-ray detector 120 based on the collected location information of the object ob (operation S41).

The calculated movement location information may be directly transmitted to the corresponding element, i.e., at least one of the X-ray emitter 110 and the X-ray detector 120. In this case, the X-ray emitter 110 or the X-ray detector 120 that has received the corresponding movement location information is moved according to the transmitted movement location information.

Thus, in some cases, the X-ray imaging apparatus 10 may generate a movement command based on the movement location information (operation S42). The generated movement command is transmitted to the corresponding element, i.e., the X-ray emitter 110 or the X-ray detector 120 (operation S43), and the X-ray emitter 110 or the X-ray detector 120 is moved according to the transmitted movement command (operation S44).

As illustrated in FIG. 16, collection of location information on the object ob by the location information collector 20 may include, in particular, sensing the object ob by the location information collector 20, e.g., a 3D sensor (operation S401) and generating 3D location information on the sensed object ob (operation S402).

According to another exemplary embodiment as illustrated in FIG. 17, collection of location information on the object ob by the location information collector 20 may include, in particular, imaging the object ob with a marker formed on an outer surface thereof using the location information collector 20, e.g., a marker identification sensor (operation S403), identifying the marker formed on the object ob (operation S404), and generating location information on the object ob using the identified marker (operation S405). Meanwhile, when the object ob is imaged by identifying a marker, the marker may be a cause of noise in an X-ray image according to radiography and thus, after identification of the marker is completed, the marker may be directly removed by a user of the X-ray imaging apparatus 10, e.g., a radiologist or the object ob, e.g., a patient. When, right before, or after the marker is removed, the X-ray emitter 110 or the X-ray detector 120 is moved according to transmitted movement command and performs X-ray imaging of the object ob (operation S44 in FIG. 15).

As is apparent from the above description, according to an X-ray imaging apparatus and a control method thereof, a movement location(s) of an X-ray emitter and/or an X-ray detector may be automatically determined.

In this case, locations of the X-ray emitter and the X-ray detector may be determined according to a location of an object and thus X-ray imaging may be implemented under optimum viewing conditions.

In addition, inconvenience of manual operation of the X-ray emitter is decreased, and delay in radiographic time generated according to the manual operation is shortened.

Moreover, movement of both the X-ray emitter and the X-ray detector may be controlled together by transmitting movement location information on both the X-ray emitter and the X-ray detector or a control command for both of them to be moved to a specific position.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An X-ray imaging apparatus comprising:
   an X-ray emitter configured to irradiate an object with X-rays and be independently movable with respect to an X-ray detector of the X-ray imaging apparatus;
   the X-ray detector configured to detect X-rays having passed through the object, convert the detected X-rays into an electric signal, and be independently movable with respect to the X-ray emitter;
   a location information collector configured to collect location information regarding the object; and
   a controller configured to execute a computer program stored in a computer readable medium,
   wherein the computer program is provided to perform controlling the X-ray emitter or the X-ray detector based on the location information regarding the object collected by the location information collector, by determining a first movement location of one of the X-ray emitter and the X-ray detector, and using the determined first movement location to determine a second movement location of a remaining one of the X-ray emitter and the X-ray detector after the first one of the X-ray emitter and the X-ray detector moves to the first movement location.

2. The X-ray imaging apparatus according to claim 1, wherein the location information regarding the object is a location of the object in a three-dimensional coordinate system.

3. The X-ray imaging apparatus according to claim 1, wherein the location information collector is a three-dimensional sensor to sense the object.

4. The X-ray imaging apparatus according to claim 1, wherein the location information collector collects location information regarding the object by identifying a marker on the object.

5. The X-ray imaging apparatus according to claim 1, wherein the location information collector is at least one of a range sensor, a three-dimensional (3D) camera, a 3D depth camera, a 3D color/depth camera, a stereo camera, an infrared camera, and a position sensitive device (PSD).

6. The X-ray imaging apparatus according to claim 1, wherein the controller controls the X-ray emitter or the X-ray detector by transmitting one of first movement location information on the X-ray emitter and second movement location information on the X-ray detector to the X-ray emitter or the X-ray detector or by generating one of a first movement command based on the first movement location information and a second movement command based on the second movement location information, and transmitting the generated one of the first and the second movement command to the X-ray emitter or the X-ray detector.

7. The X-ray imaging apparatus according to claim 6, wherein the controller transmits the one of the first and the second movement location information or one of the first and the second movement command of the X-ray emitter or the X-ray detector to the X-ray emitter or the X-ray detector using a wired communication network or a wireless communication network.

8. The X-ray imaging apparatus according to claim 6, wherein the computer program is further provided to perform generating the first movement command for the X-ray emitter based on the first movement location information on the X-ray emitter or the second movement command for the X-ray detector based on the second movement location information on the X-ray detector.

9. The X-ray imaging apparatus according to claim 1, further comprising an input unit configured to receive data or a command.

10. The X-ray imaging apparatus according to claim 9, wherein the computer program is further provided to perform calculating a first movement location information of the X-ray emitter and a second movement location information of the X-ray detector using user input information input via the input unit and the location information of the object collected by the location information collector.

11. The X-ray imaging apparatus according to claim 10, wherein the user input information comprises at least one from among a radiographic location and a radiographic range of the object to be X-ray imaged by a user, unique information of the object, information on a marker to be identified, setting information for operation of the X-ray imaging apparatus or the location information collector, and location information of the object.

12. The X-ray imaging apparatus according to claim 9, wherein the input unit transmits at least one input movement location to the controller using a wired communication network or a wireless communication network.

13. The X-ray imaging apparatus according to claim 1, wherein the computer program is further provided to perform determining a first movement location information of the X-ray emitter based on the location information of the object collected by the location information collector and determining a second movement location information of the X-ray detector using the determined first movement location information of the X-ray emitter, or determining the second movement location information of the X-ray detector based on the location information of the object collected by the location information collector and determining the first movement location information of the X-ray emitter using the determined second movement location information of the X-ray detector.

14. The X-ray imaging apparatus according to claim 1, wherein the computer program is further provided to perform determining a second movement location information of the X-ray detector based on the location information of the object collected by the location information collector and a first movement location information of the X-ray emitter, or determining the first movement location information of the X-ray emitter based on the location information of the object collected by the location information collector and the second movement location information of the X-ray detector.

15. The X-ray imaging apparatus according to claim 14, wherein the first movement location information of the X-ray emitter or the second movement location information of the X-ray detector, used to calculate a movement location of the X-ray detector or a movement location of the X-ray emitter, is input by a user.

16. A method of controlling an X-ray imaging apparatus, the method comprising:

collecting location information of the object, by a location information collector;

determining a first movement location of one of a movable X-ray emitter and a movable X-ray detector based on the location information of the object collected by the location information collector;

moving the one of the movable X-ray emitter or the movable X-ray detector according to the determined first movement location; and determining a second movement location of a remaining one of the movable X-ray emitter and the movable X-ray detector based on the first movement location of the one of the movable X-ray emitter and the movable X-ray detector after the one of the movable X-ray emitter and the movable X-ray detector moves to the first movement location.

17. The method according to claim 16, wherein the location information collector is a 3D sensor configured to sense the object, and the collecting is performed by sensing the object, the sensing being performed by the 3D sensor, generating three-dimensional location information regarding the sensed object, and collecting the generated three-dimensional location information.

18. The method according to claim 16, wherein the location information collector is a marker identification sensor configured to identify a marker formed on the object, and the collecting is performed such that the marker identification sensor identifies the marker formed on the object and location information regarding the object is calculated using the identified marker.

19. The method according to claim 16, wherein the moving comprises:

generating one of a first movement control command for the X-ray emitter and a second movement control command for the X-ray detector based on the determined first movement location and the determined second movement location;

transmitting the generated one of the first and the second movement control command to the X-ray emitter or the X-ray detector; and moving the X-ray emitter or the X-ray detector according to the transmitted one of the first and the second movement control command.

20. The method according to claim 16, wherein the method further comprises:

moving the X-ray emitter or the X-ray detector according to the determined second movement location of the remaining one of the X-ray emitter and the X-ray detector.

* * * * *